(12) United States Patent
Ohashi et al.

(10) Patent No.: US 6,607,563 B2
(45) Date of Patent: Aug. 19, 2003

(54) HAIR DYE COMPOSITION

(75) Inventors: Yukihiro Ohashi, Sumida-ku (JP);
Hajime Miyabe, Sumida-ku (JP);
Kenichi Matsunaga, Sumida-ku (JP);
Shintaro Totoki, Sumida-ku (JP);
Yoshinori Saito, Sumida-ku (JP)

(73) Assignee: Kao Corporation, Tokyo (JP)

( * ) Notice: Subject to any disclaimer, the term of this patent is extended or adjusted under 35 U.S.C. 154(b) by 130 days.

(21) Appl. No.: 09/887,437

(22) Filed: Jun. 25, 2001

(65) Prior Publication Data
US 2002/0032935 A1 Mar. 21, 2002

(30) Foreign Application Priority Data
Jun. 27, 2000 (JP) ........................................ 2000-193182

(51) Int. Cl.$^7$ ................................................ A61K 7/13
(52) U.S. Cl. ........................ 8/405; 8/471; 8/531; 8/922; 8/924; 534/753
(58) Field of Search ............................ 8/405, 411, 531, 8/922, 924; 534/753

(56) References Cited

U.S. PATENT DOCUMENTS

| 3,899,478 | A | | 8/1975 | Fleckenstein et al. ....... 260/156 |
| 4,082,740 | A | | 4/1978 | Mohr et al. ................. 260/146 |
| 5,446,136 | A | * | 8/1995 | Pape et al. .................. 534/753 |

(List continued on next page.)

FOREIGN PATENT DOCUMENTS

| DE | 1 569 648 | | 5/1970 | |
| DE | 1569648 | * | 5/1970 | ........... C09B/23/10 |
| DE | 23 47 756 | | 4/1975 | |

(List continued on next page.)

Primary Examiner—Mark Kopec
Assistant Examiner—Eisa Elhilo
(74) Attorney, Agent, or Firm—Oblon, Spivak, McClelland, Maier & Neustadt, P.C.

(57) ABSTRACT

Provided is a hair dye composition containing a direct dye A—D=D—B. This hair dye composition has markedly high hair dyeing power, has less color fade over time and undergoes a small change in the color tone of the dye even after storage.

A represents any one of the following groups (2) to (8):

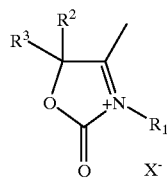

(2)

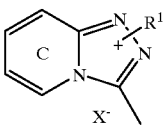

(3)

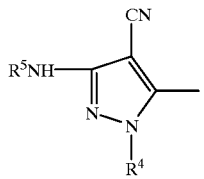

(4)

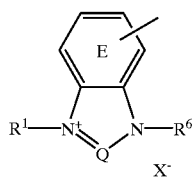

(5)

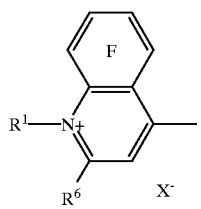

(6)

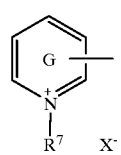

(7)

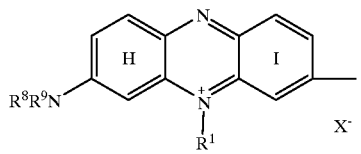

(8)

(in which $R^1$, $R^4$, $R^5$ and $R^6$ each represents H, (substituted) $C_{1-6}$ alkyl group, etc., $R^2$ and $R^3$ each represents (substituted) $C_{1-6}$ alkyl group, etc., or form, when taken together with the adjacent C, a cycloalkane ring, Q represents N or group CR', $R^7$ represents (substituted) aralkyl group or a group $CH_2$—CH(OH)—$CH_2$—OR'', $R^8$ and $R^9$ each represents H, (substituted) $C_{1-6}$ alkyl, etc., or form, when taken together with the adjacent N, a heterocycle, $X^-$ represents an anion, and rings C–I may each have a further substituent or a condensed ring), D represents N or group CR''', and B represents the residue of a coupling component.

14 Claims, No Drawings

U.S. PATENT DOCUMENTS

| | | | |
|---|---|---|---|
| 5,502,172 A | 3/1996 | Pape et al. | 534/591 |
| 5,733,343 A | 3/1998 | Mockli | 8/426 |
| 5,879,412 A * | 3/1999 | Rondeau et al. | 8/411 |
| 5,888,252 A | 3/1999 | Mockli | 8/426 |
| 5,980,587 A | 11/1999 | Samain | 8/426 |

FOREIGN PATENT DOCUMENTS

| | | | | |
|---|---|---|---|---|
| GB | 2 054 630 | | 2/1981 | |
| GB | 2054630 | * | 2/1981 | C09B/29/036 |
| JP | 49-54685 | | 5/1974 | |
| JP | 49-54686 | | 5/1974 | |
| JP | 49-54687 | | 5/1974 | |
| JP | 51-109024 | | 9/1976 | |
| JP | 5613280 | * | 10/1981 | C09B/44/12 |
| JP | 56-134280 | | 10/1981 | |
| JP | 6-271435 | | 9/1994 | |
| JP | 7-224230 | | 8/1995 | |
| JP | 8-501322 | | 2/1996 | |
| JP | 8-507545 | | 8/1996 | |
| JP | 10-502946 | | 3/1998 | |
| JP | 10-194942 | | 7/1998 | |

* cited by examiner

HAIR DYE COMPOSITION

TECHNICAL FIELD

The present invention relates to a hair dye composition having markedly high dyeing power, can strongly impart the hair with an extremely vivid color ranging from yellow, red, purple to blue, has less color fade over time and undergoes a small change in the color tone of the dye even after storage.

BACKGROUND ART

Hair dyes can be classified by the dye to be used therefor, or whether they have bleaching action of melanin or not. Typical examples include a two-part permanent hair dye composed of a first part containing an alkali agent, an oxidation dye and a direct dye such as nitro dye and a second part containing an oxidizing agent; and one-part semi-permanent hair dye containing an organic acid or an alkali agent, and a direct dye such as acid dye, basic dye or nitro dye.

The above-described permanent hair dye is however accompanied with the drawbacks that color tone imparted by an oxidation dye is not so vivid and the color of the hair dyed with a vivid-color producing nitro dye ordinarily employed as a direct dye markedly fades over time and becomes dull soon even if the color tone rightly after dyeing is very vivid (Japanese Patent Application Laid-open (Kokai) No. Hei 6-271435).

Recently, hair dyes containing as a direct dye a so-called cationic dye having a cation group contained in their conjugate system have been reported (Japanese Language Laid-Open Publication (PCT) No. Hei 8-507545, 8-501322 or 10-502946, or Japanese Patent Application Laid-Open (Kokai) No. Hei 10-194942). They have been found to involve drawbacks that intended dyeing effects are not available owing to decomposition of them caused by mixing, upon hair dyeing, with hydrogen peroxide ordinarily employed as an oxidizing agent; and that they are unstable to an alkali agent or a reducing agent essentially contained in a permanent hair dye.

DISCLOSURE OF THE INVENTION

An object of the present invention is to provide a hair dye composition which has high hair dyeing power, less color fade over time, and excellent storage stability to permit only a small change in color tone of the dye after storage.

The present inventors have found that when the below-described compound which is known, as a dye for dyeing and printing therewith fiber materials, paper or leather, in Offenlegungsschrift DE-1569648, UK Patent Application GB 2054630, Japanese Patent Application Laid-Open (Kokai) Nos. Hei 7-224230, Sho 51-109024 and Sho 56-134280, Offenlegungsschrift DE 2347756, Japanese Patent Applications Laid-Open Nos. Sho 49-54685, Sho 49-54686 and Sho 49-54687, or as Basic Blue 16 and Basic Black 2 is used as a hair dye, the resulting dye composition can strongly impart the hair with a vivid color ranging from yellow, red, purple to blue without decomposing the dye upon hair dyeing, exhibits excellent light resistance, washing resistance, perspiration resistance, friction resistance and heat resistance, and undergoes a small change in the color tone of the dye after storage as compared with that rightly after preparation because the dye exists in the composition stably.

In one aspect of the present invention, there is thus provided a hair dye composition comprising, as a direct dye, a compound represented by the following formula (1):

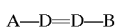  (1)

wherein, A represents a group of the following formula (2), (3), (4), (5), (6), (7) or (8):

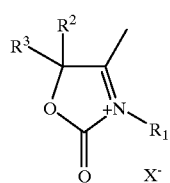  (2)

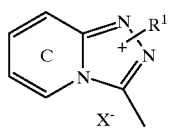  (3)

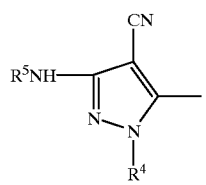  (4)

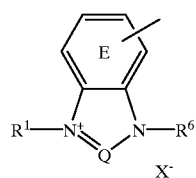  (5)

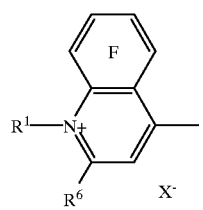  (6)

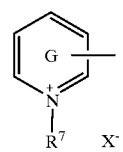  (7)

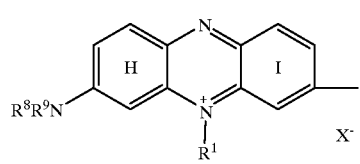  (8)

(in which, $R^1$ and $R^6$ each independently represents a $C_{1-6}$ alkyl group which may have a substituent, an alkenyl group which may have a substituent or an aryl group which may have a substituent, $R^2$ and $R^3$ each independently represents a $C_{1-6}$ alkyl group which may have a substituent, an alkenyl group which may have a substituent, an aryl group which may have a substituent, or $R^2$ and $R^3$, when taken together with the adjacent carbon atom, form a 5- to 7-membered cycloalkane ring, $R^4$ represents a hydrogen atom, a $C_{1-6}$ alkyl group which may have a substituent, an alkenyl group which may have a substituent, or an aryl group which may have a substituent, $R^5$ represents a hydrogen atom, a $C_{1-6}$ alkyl group which may have a substituent, an alkenyl group which may have a substituent, an aryl group which may have a substituent, an acyl group, an alkoxycarbonyl group, a carbamoyl group, an alkylsulfonyl group or an arylsulfonyl group, Q represents a nitrogen atom or a group CR' (in which R' represents a hydrogen atom, a $C_{1-6}$ alkyl group which may have a substituent, an alkenyl group which may have a substituent or an aryl group which may have a substituent), $R^7$ represents an aralkyl group which may have a substituent or a group $CH_2$—CH(OH)—$CH_2$—OR" (in which R" represents a $C_{1-6}$ alkyl group which may have a substituent, an alkenyl group which may have a substituent or an aryl group which may have a substituent), $R^8$ and $R^9$ each independently represents a hydrogen atom, a $C_{1-6}$ alkyl group which may have a substituent, an alkenyl group which may have a substituent or an aryl group which may have a substituent, or $R^8$ and $R^9$, when taken together with the adjacent nitrogen atom, form a nitrogen-containing heterocycle, $X^-$ represents an anion, and rings C, E, F, G, H and I may each independently have a further substituent or may be cyclocondensed with another aromatic ring), D represents a nitrogen atom or a group CR''' (in which R''' represents a hydrogen atom or a $C_{1-6}$ alkyl group which may have a substituent), and B represents the residue of a phenol, aniline, acylacetoarylamide, pyridone, quinoline, isoquinoline, pyrazole, indole, diphenylamine, aminopyridine, pyrimidine, pyrimidone, naphthol, naphthylamine, aminothiazole, thiophene or hydroxypyridine type coupling component.

In another aspect of the present invention, there is also provided a method for dyeing the hair with the above-described hair dye composition.

BEST MODE FOR CARRYING OUT THE INVENTION

Examples of the $C_{1-6}$ alkyl group represented by $R^1$, $R^2$, $R^3$, $R^4$, $R^5$, $R^6$, $R^8$, $R^9$, R', R" or R''' include methyl, ethyl, propyl, isopropyl and cyclohexyl groups; those of the alkenyl group include vinyl, allyl and isobutenyl groups; and those of the aryl group include phenyl and naphthyl groups, each of which may be substituted by an aryl group, cyano group, halogen atom, hydroxyl group, $C_{1-4}$ alkoxy group, $C_{1-4}$ hydroxyalkoxy group, alkoxycarbonyl group, heterocyclic group, group $NR^{10}R^{11}$ (in which $R^{10}$ and $R^{11}$ each independently represents a hydrogen atom, a $C_{1-6}$ alkyl group which may have a substituent or an aryl group which may have a substituent).

Examples of the cycloalkane ring formed by $R^2$ and $R^3$ when they are taken together with the adjacent carbon atom include cyclopentane, cyclohexane and cycloheptane rings.

Examples of the acyl group represented by $R^5$ include formyl, acetyl and propionyl groups, those of the alkoxycarbonyl group include methoxycarbonyl and ethoxycarbonyl groups; those of the alkylsulfonyl group include methanesulfonyl group; and those of the arylsulfonyl group include benzenesulfonyl and toluenesulfonyl groups.

Examples of the aralkyl group represented by $R^7$ include benzyl and phenethyl groups.

Examples of the nitrogen-containing heterocycle formed by $R^8$ and $R^9$ when they are taken together with the adjacent nitrogen atom include pyrrolidine, piperidine, morpholine and piperazine rings, each of which may be substituted by an alkyl group.

Examples of the substituent which an aralkyl group represented by $R^7$ or the ring C, E, F, G or H may have include alkyl groups, aryl groups, alkoxy groups, amino group, mono- or di-alkylamino groups, hydroxy group, cyano group, nitro group, acylamino groups, halogen atoms and alkoxycarbonyloxy groups, more specifically, methyl, ethyl, methoxy, ethoxy, chlorine and bromine. As another aromatic ring with which the above-described ring may be cyclocondensed, the benzene ring may be given as an example.

Examples of the anion represented by $X^-$ include chloride ions, bromide ions, iodide ions, trichlorozincic acid ions, tetrachlorozincic acid ions, sulfuric acid ions, hydrosulfuric acid ions, methyl sulfate ions, phosphoric acid ions, formic acid ions and acetic acid ions.

Examples of the residue of a coupling component represented by B include those represented by the following formulas:

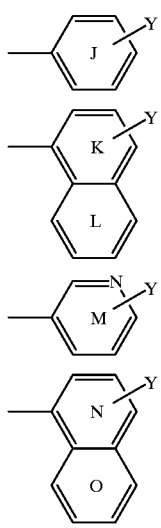

wherein, Y represents a hydroxy group or a group —$NR^{12}R^{13}$ (in which $R^{12}$ and $R^{13}$ each independently represents a hydrogen atom, a $C_{1-6}$ alkyl group which may have a substituent, an alkenyl group which may have a substituent or an aryl group which may have a substituent, or $R^{12}$ and $R^{13}$, when taken together with the adjacent nitrogen atom, form a nitrogen-containing heterocycle), and rings J, K, L, M, N and O may each have a further substituent.

As the alkyl, alkenyl and aryl groups represented by $R^{12}$ or $R^{13}$, and substituents therefor, nitrogen-containing heterocyclic group formed by them, and substituents for the rings J to O, those similar in the above-described group A can be given as examples.

Specific examples of the direct dye (1) to be used in the present invention will next be shown.

Compound (a)
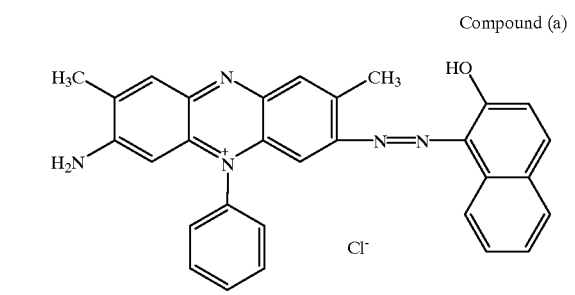
Compound (b)
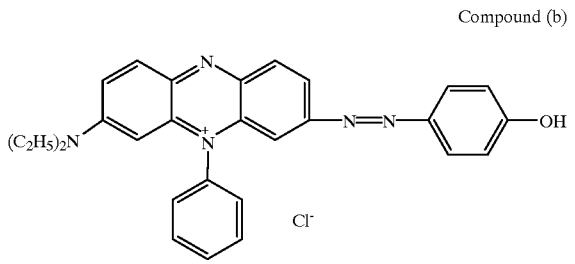
Compound (c)
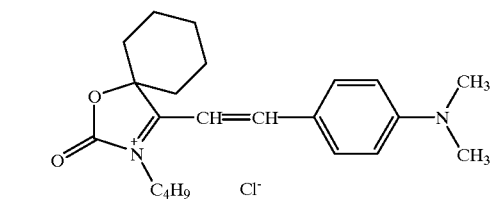
Compound (d)
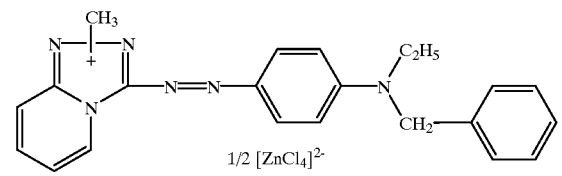
Compound (e)
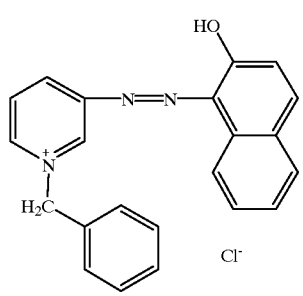
Compound (f)
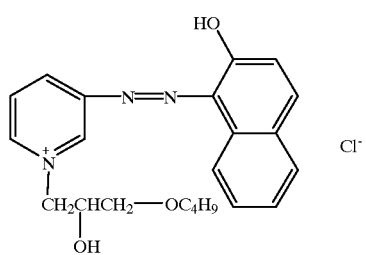
Compound (g)
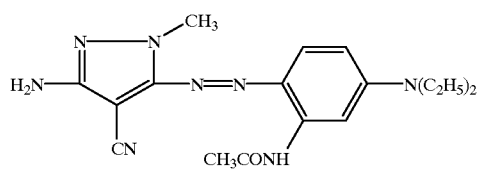
Compound (h)
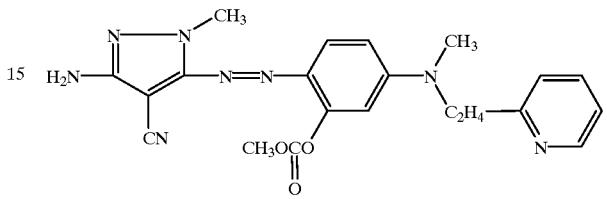
Compound (i)
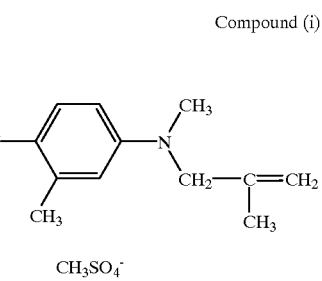
Compound (j)
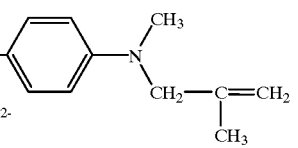
Compound (k)
Compound (l)
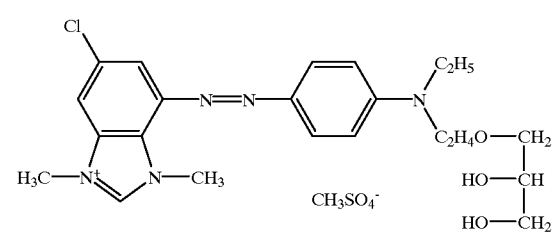

-continued

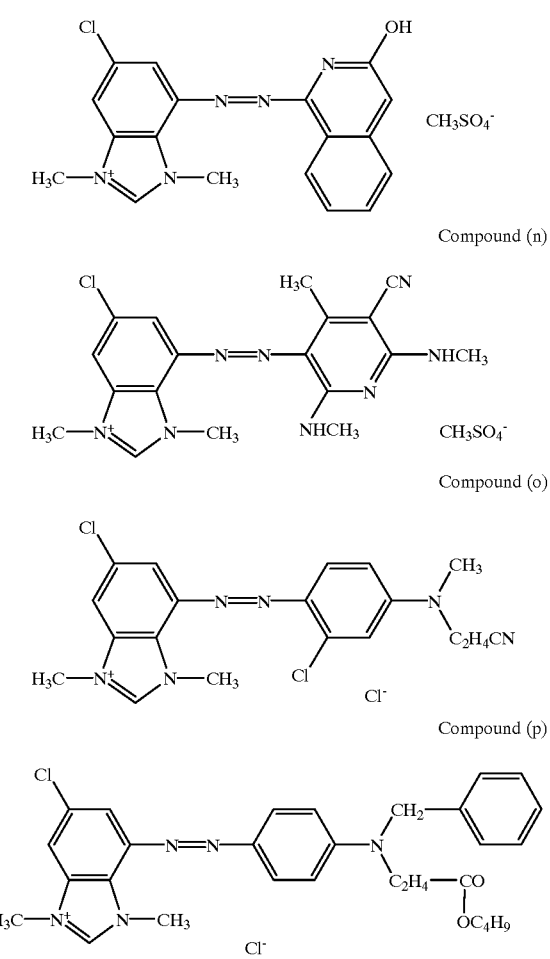

Compound (m)

Compound (n)

Compound (o)

Compound (p)

As a direct dye, at least one of these direct dyes (1) can be used or another direct dye can be used in combination therewith. In particular, when the direct dye (1) is a yellow dye, combination with red and blue dyes, when the direct dye is a red dye, combination with yellow and blue dyes, and when the direct dye (1) is a blue dye, combination with yellow and red dyes each makes it possible to dye the hair with a deep and highly lustrous dark brown or black color.

Examples of the direct dye other than the direct dyes (1) include Basic Blue 7 (C.I. 42595), Basic Blue 26 (C.I. 44045), Basic Blue 99 (C.I. 56059), Basic Violet 10 (C.I. 45170), Basic Violet 14 (C.I. 42515), Basic Brown 16 (C.I. 12250), Basic Brown 17 (C.I. 12251), Basic Red 2 (C.I. 50240), Basic Red 22 (C.I. 11055), Basic Red 76 (C.I. 12245), Basic Red 118 (C.I. 12251:1) and Basic Yellow 57 (C.I. 12719); and basic dyes as described in Japanese Patent Publication No. Sho 58-2204, Japanese Patent Application Laid-Open (Kokai) No. Hei 9-118832, Japanese Language Laid-Open Publication (PCT) No. Hei 8-501322 or Japanese Language Laid-Open Publication (PCT) No. Hei 8-507545.

The direct dye (1) is preferably added in an amount of 0.01 to 20 wt. %, more preferably 0.05 to 10 wt. %, especially 0.1 to 5 wt. % based on the whole composition (after mixture of all the component parts when the hair dye composition is a two part or three part type; this will apply equally hereinafter). When another direct dye is added in combination, the content of it in total with the direct dye (1) preferably ranges from 0.05 to 10 wt. %, especially 0.1 to 5 wt. %.

The hair dye composition of the present invention is preferably adjusted to pH 6 to 11, with pH 8 to 11 being especially preferred. Examples of the alkali agent to be used for pH adjustment include ordinarily employed ones such as ammonia, organic amines and salts thereof. The alkali agent is preferably added in an amount of 0.01 to 20 wt. %, more preferably 0.1 to 10 wt. %, especially 0.5 to 5 wt. % based on the whole composition.

In the hair dye composition of the present invention, an oxidizing agent can be incorporated. In this case, hair dyeing and bleaching can be carried out simultaneously, which facilitates more vivid hair dyeing. Ordinarily employed oxidizing agents, for example, hydrogen peroxide, persulfates such as ammonium persulfate, potassium persulfate and sodium persulfate, perborates such as sodium perborate, percarbonates such as sodium percarbonate and bromates such as sodium bromate and potassium bromate are usable. Out of them, hydrogen peroxide is especially preferred. The oxidizing agent is preferably added in an amount of 0.5 to 10 wt. %, especially 1 to 8 wt. %, based on the whole composition.

In the hair dye composition of the present invention, an oxidation dye can be incorporated further. This incorporation enables markedly vivid dyeing not attainable by the single use of an oxidation dye. In this case, the above-exemplified oxidizing agents can be used as an oxidizing agent, with hydrogen peroxide being particularly preferred. Alternatively, an oxidizing enzyme such as laccase can be employed. For the oxidation dye, known color developers and couplers ordinarily employed for an oxidation type hair dye can be used.

Examples of the developer include p-phenylenediamines having one or several groups selected from groups $NH_2$—, NHR— and $NR_2$— (in which R represents a $C_{1-4}$ alkyl group or a hydroxyalkyl group) such as p-phenylenediamine, p-toluylenediamine, N-methyl-p-phenylenediamine, chloro-p-phenylenediamine, 2-(2'-hydroxyethylamino)-5-aminotoluene, N,N-bis-(2-hydroxyethyl)-p-phenylenediamine, 2-hydroxyethyl-p-phenylenediamine, 2,6-dimethyl-p-phenylenediamine, methoxy-p-phenylenediamine, 2,6-dichloro-p-phenylenediamine, 2-chloro-6-methyl-p-phenylenediamine, 6-methoxy-3-methyl-p-phenylenediamine, 2,5-diaminoanisole, N-(2-hydroxypropyl)-p-phenylenediamine and N-2-methoxyethyl-p-phenylenediamine; 2,5-diaminopyridine derivatives and 4,5-diaminopyrazole derivatives; p-aminophenols such as p-aminophenol, 2-methyl-4-aminophenol, N-methyl-p-aminophenol, 3-methyl-4-aminophenol, 2,6-dimethyl-4-aminophenol, 3,5-dimethyl-4-aminophenol, 2,3-dimethyl-4-aminophenol and 2,5-dimethyl-4-aminophenol; o-aminophenols, o-phenylenediamines, 4,4'-diaminophenylamine and hydroxypropylbis(N-hydroxyethyl-p-phenylenediamine); and salts thereof.

Examples of the coupler include 1-naphthol, 1,5-dihydroxynaphthalene, 1,7-dihydroxynaphthalene, 2,7-dihydroxynaphthalene, 5-amino-2-methylphenol, 5-(2'-hydroxyethylamino)-2-methylphenol, 2,4-diaminoanisole, m-toluylenediamine, resorcin, m-phenylenediamine, m-aminophenol, 4-chlororesorcin, 2-methylresorcin, 2,4-diaminophenoxyethanol, 2,6-diaminopyridine, 2-amino-3-hydroxypyridine, 4-hydroxyindole, 6-hydroxyindole, 2,4-diamino-6-hydroxypyrimidine, 2,4,6-triaminopyrimidine, 2-amino-4,6-dihydroxypyrimidine, 4-amino-2,6-dihydroxypyrimidine, 4,6-diamino-2-hydroxypyrimidine and 1,3-bis(2,4-diaminophenoxy)propane; and salts thereof.

As each of a developer and a coupler, at least one of the above-exemplified ones can be used. Each of them is preferably added in an amount of 0.01 to 20 wt. %, especially 0.5 to 10 wt. % based on the whole composition.

To the hair dye composition of the present invention, a known autoxidation dye typified by an indole or an indoline, or a known direct dye such as a nitro dye or a disperse dye can also be added.

When an anionic component (such as anionic surfactant or anionic polymer) is added to the hair dye composition of the present invention in the case where the direct dye (1) is cationic, it is preferred to satisfy the following equation:

"Ion activity concentration of the anionic component/ion activity concentration of the cationic direct dye (1)≦8"

The term "ion activity concentration" as used herein means "molar concentration×ionic valence".

Addition of a polyol, polyol alkyl ether, cationic or amphoteric polymer or silicone to the hair dye composition of the present invention is preferred, because the resulting composition can dye the hair uniformly and has improved cosmetic effects of the hair.

In addition to the above-described components, those ordinarily employed as a raw material for cosmetics can be added to the hair dye composition of the present invention. Examples of such an optional component include hydrocarbons, animal or vegetable fats and oils, higher fatty acids, organic solvents, penetration promoters, cationic surfactants, natural or synthetic polymers, higher alcohols, ethers, amphoteric surfactants, nonionic surfactants, protein derivatives, amino acids, antiseptics, chelating agents, stabilizing agents, antioxidants, plant extracts, crude drug extracts, vitamins, colorants, perfumes and ultraviolet absorbers.

The hair dye composition of the present invention can be prepared in a conventional manner into a one-part composition, a two-part composition having a first component part containing an alkali agent and a second component part containing an oxidizing agent, or a three-part composition having, in addition to these two component parts, a powdery oxidizing agent such as persulfate. The direct dye (1) can be incorporated in either one or both of these component parts of the two-part or three-part composition. When the hair dye composition of the present invention is one-part type, it is applied to the hair directly, while the two- or three-part type is applied to the hair after mixing these parts upon hair dyeing.

No particular limitation is imposed on the form of the hair dye composition of the present invention. Examples include powder, transparent liquid, emulsion, cream, gel, paste, aerosol, and aerosol foam. It preferably has a viscosity of 2000 to 100000 mPa·s in the stage of application to the hair (after mixing of all the components when the hair dye composition is a two-part or three-part type).

EXAMPLES

Examples 1 to 5

In a manner known per se in the art, hair dyes as shown in Table 1 were prepared.

TABLE 1

|  | Examples | | | | |
| --- | --- | --- | --- | --- | --- |
| (wt. %) | 1 | 2 | 3 | 4 | 5 |
| Dye [Compound (a)] | 0.2 |  | 0.15 | 0.1 | 0.2 |
| Dye [Compound (b)] |  | 0.5 |  | 0.1 |  |
| Dye [Compound (c)] |  | 0.3 |  | 0.1 | 0.2 |
| Dye [formula (I), Red] |  |  | 0.15 |  | 0.05 |
| Dye [formula (II), Yellow] |  |  | 0.1 | 0.1 |  |
| Ethanol |  | 5 |  | 5 | 5 |
| Propylene glycol |  |  | 5 |  | 5 |
| Diethylene glycol monoethyl ether |  | 10 |  |  |  |
| Guar gum | 1 |  |  |  |  |
| Hydroxypropyl guar gum |  | 1 | 1 | 1 | 1 |
| "Gufquat 734" (trade name; product of ISP Japan) | 1 |  | 1 |  |  |
| "Catinal LC100" (trade name; product of Toho Chemical Industry) |  | 1 |  |  | 1 |
| "Polyether-modified silicone KF6005" (trade name; product of Shin-Etsu Chemical) |  |  |  |  | 0.4 |
| "Amodimethicone SM8702C" (trade name; product of Dow Corning Toray Silicone) |  |  |  | 1.5 |  |
| Monoethanolamine | 0.1 | | | | |
| Phosphoric acid | Amount to adjust pH to 9 | | | | |
| Perfume | q.s. | | | | |
| Water | Balance | | | | |

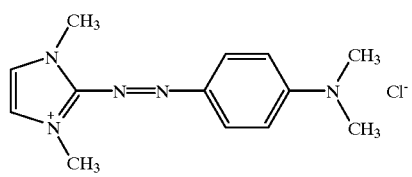

(I)

TABLE 1-continued

|  | Examples | | | | |
|---|---|---|---|---|---|
| (wt. %) | 1 | 2 | 3 | 4 | 5 |

(II)

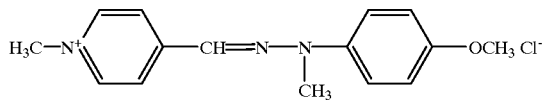

Examples 6 to 9

In a manner known per se in the art, hair dyes as shown in Table 2 were prepared.

TABLE 2

| | | Examples | | | |
|---|---|---|---|---|---|
| (wt. %) | | 6 | 7 | 8 | 9 |
| 1st part | Dye [Compound (a)] | 0.2 | | 0.15 | 0.2 |
| | Dye [Compound (d)] | | 0.1 | 0.15 | |
| | Dye [Compound (e)] | | 0.1 | 0.15 | |
| | Dye [formula (I), Red] | | 0.1 | | 0.05 |
| | 28 wt % Aqueous ammonia | | 5 | | |
| | Monoethanolamine | | 2 | | |
| | Propylene glycol | | 8 | | |
| | Polyoxyethylene 20 isostearyl ether | | 24 | | |
| | Polyoxyethylene (2) isostearyl ether | | 20 | | |
| | "Merquat 280" (trade name; product of Calgon Corp., a 35 wt. % aqueous solution) | | 8 | | |
| | "Polymer JR400" (trade name; product of Union Carbide) | 0.5 | | 0.5 | |
| | "Amodimethicone SM8702C" (trade name; product of Dow Corning Toray Silicone) | | 2 | | |
| | "Polyether modified silicone KF6005" (trade name; product of Shin-Etsu Chemical) | | | | 0.3 |
| | Tetrasodium ethylenediaminetetraacetate | | 0.1 | | |
| | Perfume | | q.s. | | |
| | Ammonium chloride | | Amount to adjust pH to 10 | | |
| | Water | | Balance | | |
| 2nd part | 35 wt. % Aqueous hydrogen peroxide | | 17.1 | | |
| | Methylparaben | | 0.1 | | |
| | Phosphoric acid | | Amount to adjust pH to 3.5 | | |
| | Water | | Balance | | |

Examples 10 to 12

In a manner known per se in the art, hair dyes as shown in Table 3 were prepared.

TABLE 3

| | | Examples | | |
|---|---|---|---|---|
| (wt. %) | | 10 | 11 | 12 |
| 1st part | Toluene-2,5-diamine | 1.9 | 1 | |
| | Para-aminophenol | | | 1 |
| | Resorcin | 2 | | |
| | Para-amino-ortho-cresol | | | 1.1 |
| | 2,4-Diaminophenoxyethanol | | 1.37 | |
| | Dye [Compound (f)] | 0.05 | | |
| | Dye [Compound (g)] | | 0.15 | |

TABLE 3-continued

| | | Examples | | |
|---|---|---|---|---|
| (wt. %) | | 10 | 11 | 12 |
| | Dye (Compound (k))] | | | 0.1 |
| | 28 wt. % Aqueous ammonia | | 5 | |
| | Monoethanolamine | | 2 | |
| | Propylene glycol | | 8 | |
| | Polyoxyethylene (20) isostearyl ether | | 24 | |
| | Polyoxyethylene (2) isostearyl ether | | 20 | |
| | "Merquat 280" (trade name; product of Calgon Corp., a 35 wt. % aqueous solution) | 8 | | |
| | "Polymer JR400" (trade name; product of Union Carbide) | | 0.5 | |
| | "Amodimethicone SM8702C" (trade name; product of Dow Corning Toray Silicone) | | | 2 |
| | Sodium sulfite | | 0.05 | |
| | Ascorbic acid | | 0.5 | |
| | Tetrasodium ethylenediaminetetraacetate | | 0.1 | |
| | Perfume | | q.s. | |
| | Ammonium chloride | | Amount to adjust pH to 10 | |
| | Water | | Balance | |
| 2nd part | 35 wt. % Aqueous hydrogen peroxide | | 17.1 | |
| | Methylparaben | | 0.1 | |
| | Phosphoric acid | | Amount to adjust pH to 3.5 | |
| | Water | | Balance | |

Examples 13 & 14

In a manner known per se in the art, the following hair dye was prepared.

TABLE 4

| | | Examples | |
|---|---|---|---|
| (wt. %) | | 13 | 14 |
| 1st part | Para-aminophenol | 1 | |
| | Para-amino-ortho-cresol | | 1.1 |
| | Compound (a) | 0.1 | |
| | Compound (n) | | 0.1 |
| | 28 wt. % Aqueous ammonia | 5 | |
| | Monoethanolamine | 2 | |
| | Cetanol | 8.5 | |
| | Polyoxyethylene (40) cetyl ether | 3 | |
| | Polyoxyethylene (2) cetyl ether | 3.5 | |
| | Stearyl trimethyl ammonium chloride | 2 | |
| | Liquid paraffin | 0.5 | |
| | Sodium sulfite | 0.05 | |
| | Ascorbic acid | 0.5 | |
| | Tetrasodium ethylenediaminetetraacetate | 0.1 | |
| | Perfume | q.s. | |
| | Ammonium chloride | Amount to adjust pH to 10 | |
| | Water | Balance | |

TABLE 4-continued

| (wt. %) | Examples | |
|---|---|---|
| | 13 | 14 |
| 2nd part | 35 wt. % Aqueous hydrogen peroxide | 17.1 |
| | Methylparaben | 0.1 |
| | Phosphoric acid | Amount to adjust pH to 3.5 |
| | Water | Balance |

What is claimed is:

1. A hair dye composition, comprising:

a one-part aqueous formulation containing a direct dye compound represented by formula (1):

$$A—D=D—B \quad (1)$$

wherein,

A represents a group of one of the following formulas (2), (3), (4), (5), (7) or (8):

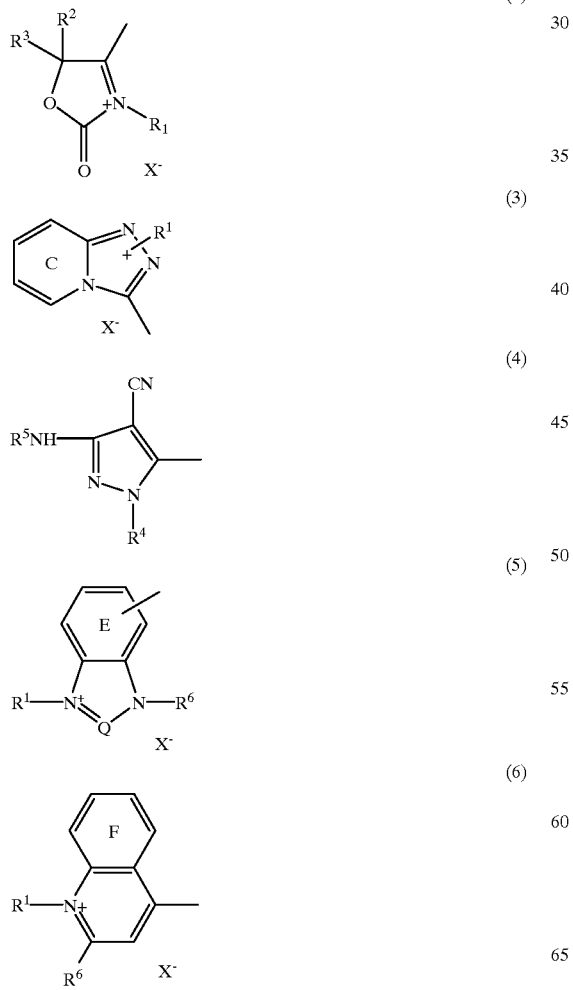

wherein $R^1$ and $R^6$ each independently represents a $C_{1-6}$ alkyl group which may have a substituent, an alkenyl group which may have a substituent or an aryl group which may have a substituent, $R^2$ and $R^3$ each independently represents a $C_{1-6}$ alkyl group which may have a substituent, an alkenyl group which may have a substituent, an aryl group which may have a substituent, $R_2$ and $R_3$ form, when taken together with the adjacent carbon atom, a 5- to 7-membered cycloalkane ring, $R^4$ represents a hydrogen atom, a $C_{1-6}$ alkyl group which may have a substituent, an alkenyl group which may have a substituent, or an aryl group which may have a substituent, $R^5$ represents a hydrogen atom, a $C_{1-6}$ alkyl group which may have a substituent, an alkenyl group which may have a substituent, an aryl group which may have a substituent, an acyl group, an alkoxycarbonyl group, a carbamoyl group, an alkylsulfonyl group or an arylsulfonyl group, Q represents a nitrogen atom or a group CR', wherein R' represents a hydrogen atom, a $C_{1-6}$ alkyl group which may have a substituent, an alkenyl group which may have a substituent or an aryl group which may have a substituent, $R^7$ represents an aralkyl group which may have substituent a group $CH_2$—CH (OH)—$CH_2$—OR," wherein R" represents a $C_{1-6}$ alkyl group which may have a substituent, an alkenyl group which may have a substituent or an aryl group which may have a substituent, $R^8$ and $R^9$ each independently represents a $C_{1-6}$ alkyl group which may have a substituent, an alkenyl group which may have a substituent or an aryl group which may have a substituent, or $R^8$ and $R^9$ form, when taken together with the adjacent nitrogen atom, a nitrogen-containing heterocycle; X represents an anion, and rings C, E, G, H and I may each independently have a substituent or may be cyclocondensed with another aromatic ring;

D represents a nitrogen atom or a group CR,'" wherein R'" represents a hydrogen atom or a $C_{1-6}$ alkyl group which may have a substituent; and B represents the residue of a phenol, aniline, acylacetoarylamide, pyridone, quinoline, isoquinoline, pyrazole, indole, diphenylamine, aminopyridine, pyrimidine, pyrimidone, naphthol, naphthylamine, amninothiazaole, thiophene or hydroxypyridine coupling component; the composition having a pH ranging from 6–11 that is adjusted to within said range by an alkali agent and containing at least one cosmetic ingredient selected from the group consisting of hydrocarbons, animal or vegetable fats and oils, fatty acids, organic solvents, hair penetration promoters, cationic surfactants, natural or synthetic polymers, alcohols, ethers, amphoteric surfactants, nonionic surfactants, protein derivatives, amino acids, antiseptics, chelating agents, stabilizing agents, antioxidants, plant extracts, crude drug extracts, vitamins, colorants, perfumes, aerosolizing agents and UV absorbers.

2. A hair dye composition, comprising:

a two-part aqueous formulation comprising, in a first part, a direct dye compound represented by formula (1):

$$A-D=D-B \qquad (1)$$

wherein,

A represents a group of one of the following formulas (2), (3), (4), (5), (7) or (8):

(2) [structure with $R^2$, $R^3$, $R_1$, $X^-$]

(3) [structure with ring C, $R^1$, $X^-$]

(4) [structure with $R^5NH$, CN, $R^4$]

(5) [structure with ring E, $R^1$, $R^6$, Q, $X^-$]

(6) [structure with ring F, $R^1$, $R^6$, $X^-$]

(7) [structure with ring G, $R^7$, $X^-$]

(8) [structure with rings H, I, $R^8R^9N$, $R^1$, $X^-$]

wherein $R^1$ and $R^6$ each independently represents a $C_{1-6}$ alkyl group which may have a substituent, an alkenyl group which may have a substituent or an aryl group which may have a substituent, $R^2$ and $R^3$ each independently represents a $C_{1-6}$ alkyl group which may have a substituent, an alkenyl group which may have a substituent, an aryl group which may have a substituent, $R^2$ and $R^3$ form, when taken together with the adjacent carbon atom, a 5- to 7-membered cycloalkane ring, $R^4$ represents a hydrogen atom, a $C_{1-6}$ alkyl group which may have a substituent, an alkenyl group which may have a substituent, or an aryl group which may have a substituent, $R^5$ represents a hydrogen atom, a $C_{1-6}$ alkyl group which may have a substituent, an alkenyl group which may have a substituent, an aryl group which may have a substituent, an acyl group, an alkoxycarbonyl group, a carbamoyl group, an alkylsulfonyl group or an arylsulfonyl group, Q represents a nitrogen atom or a group CR', wherein R' represents a hydrogen atom, a $C_{1-6}$ alkyl group which may have a substituent, an alkenyl group which may have a substituent or an aryl group which may have a substituent, $R^7$ represents an aralkyl group which may have a substituent or a group $CH_2$—CH(OH)—$CH_2$—OR," wherein R" represents a $C_{1-6}$ alkyl group which may have a substituent, an alkenyl group which may have a substituent or an aryl group which may have a substituent, $R^8$ and $R^9$ each independently represents a $C_{1-6}$ alkyl group which may have a substituent, an alkenyl group which may have a substituent or an aryl group which may have a substituent, or $R^8$ and $R^9$ form, when taken together with the adjacent nitrogen atom, a nitrogen-containing heterocycle; X represents an anion, and rings C, E, F, G, H and I may each independently have a substituent or may be cyclocondensed with another aromatic ring;

D represents a nitrogen atom or a group CR,'" wherein R'" represents a hydrogen atom or a $C_{1-6}$ alkyl group which may have a substituent; and B represents the residue of a phenol, aniline, acylacetoarylamide, pyridone, quinoline, isoquinoline, pyrazole, indole, diphenylamine, aminopyridine, pyrimidine, pyrimidone, naphthol, naphthylamine, amninothiazaole, thiophene or hydroxypyridine coupling component; the first part having a pH ranging from 6–11 that is adjusted to within said range by an alkali agent; and a second part, comprising an aqueous solution of an oxidizing agent.

3. A hair dye composition, comprising:

a three-part aqueous formulation comprising, in a first part, a direct dye compound represented by formula (1):

$$A-D=D-B \qquad (1)$$

wherein,

A represents a group of one of the following formulas (2), (3), (4), (5), (7) or (8):

(2)
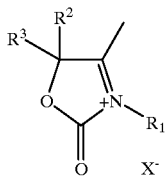

(3)
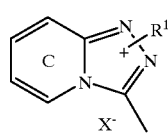

(4)
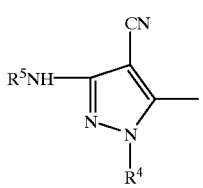

(5)
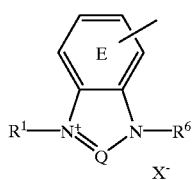

(6)
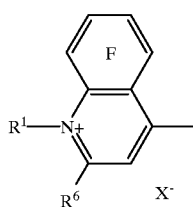

(7)
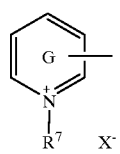

(8)
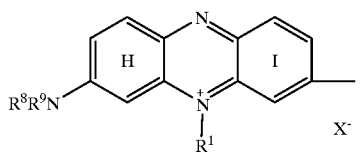

wherein $R^1$ and $R^6$ each independently represents a $C_{1-6}$ alkyl group which may have a substituent, an alkenyl group which may have a substituent or an aryl group which may have a substituent, $R^2$ and $R^3$ each independently represents a $C_{1-6}$ alkyl group which may have a substituent, an alkenyl group which may have a substituent, an aryl group which may have a substituent, $R^2$ and $R^3$ form, when taken together with the adjacent carbon atom, a 5- to 7-membered cycloalkane ring, $R^4$ represents a hydrogen atom, a $C_{1-6}$ alkyl group which may have a substituent, an alkenyl group which may have a substituent, or an aryl group which may have a substituent, $R^5$ represents a hydrogen atom, a $C_{1-6}$ alkyl group which may have a substituent, an alkenyl group which may have a substituent, an aryl group which may have a substituent, an acyl group, an alkoxycarbonyl group, a carbamoyl group, an alkylsulfonyl group or an arylsulfonyl group, Q represents a nitrogen atom or a group CR', wherein R' represents a hydrogen atom, a $C_{1-6}$ alkyl group which may have a substituent, an alkenyl group which may have a substituent or an aryl group which may have a substituent, $R^7$ represents an aralkyl group which may have a substituent or a group $CH_2$—$CH(OH)$—$CH_2$—OR," wherein R" represents a $C_{1-6}$ alkyl group which may have a substituent, an alkenyl group which may have a substituent or an aryl group which may have a substituent, $R^8$ and $R^9$ each independently represents a $C_{1-6}$ alkyl group which may have a substituent, an alkenyl group which may have a substituent or an aryl group which may have a substituent, or $R^8$ and $R^9$ form, when taken together with the adjacent nitrogen atom, a nitrogen-containing heterocycle; $X^-$ represents an anion, and rings C, E, G, H and I may each independently have a substituent or may be cyclocondensed with another aromatic ring;

D represents a nitrogen atom or a group CR,''' wherein R''' represents a hydrogen atom or a $C_{1-6}$ alkyl group which may have a substituent; and B represents the residue of a phenol, aniline, acylacetoarylamide, pyridone, quinoline, isoquinoline, pyrazole, indole, diphenylamine, aminopyridine, pyrimidine, pyrimidone, naphthol, naphthylamine, amninothiazaole, thiophene or hydroxypyridine coupling component; the first part having a pH ranging from 6–11 that is adjusted to within said range by an alkali agent;

a second part, comprising an aqueous solution of an oxidizing agent; and a third part, comprising a powdered oxidizing agent.

4. The hair dye composition according to claim 1, wherein the content of alkali in the composition ranges from 0.01 to 20 wt % of the formulation.

5. The hair dye composition according to claim 2, wherein the oxidizing agent is hydrogen peroxide, a persulfate, a perborate, a percarbonate or a bromate.

6. The hair dye composition according to claim 2, wherein the oxidizing agent is present in the entire composition in an amount of 0.5 to 10 wt %.

7. The hair dye composition according to claim 2, wherein the oxidizing agent is combined with a developer and a coupler in the second part of the composition, each present in an amount ranging from 0.01 to 20 wt % of the entire composition.

8. The hair dye composition according to claim 3, wherein the oxidizing agent of the second part is hydrogen peroxide, a persulfate, a perborate, a percarbonate or a bromate.

9. The hair dye composition according to claim 3, wherein the oxidizing agent of the second part is present in the entire composition in an amount of 0.5 to 10 wt %.

10. The hair dye composition according to claim 3, wherein the oxidizing agent is combined with a developer and a coupler in the second part of the composition, each present in an amount ranging from 0.01 to 20 wt % of the entire composition.

11. The hair dye composition according to claim 3, wherein the third part of the composition contains a powdered persulfate oxidizing agent.

12. A method of dyeing hair, comprising:

treating the hair with a one-part aqueous formulation containing a direct dye compound represented by formula (1):

A—D=D—B (1)

wherein,

A represents a group of one of the following formulas (2), (3), (4), (5), (7) or (8):

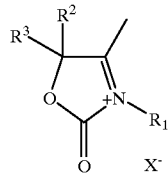

(2)

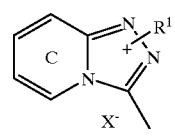

(3)

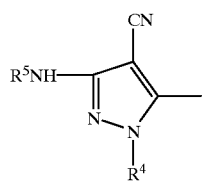

(4)

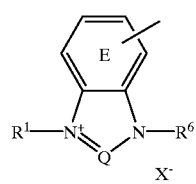

(5)

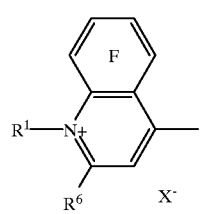

(6)

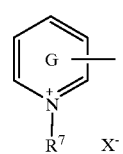

(7)

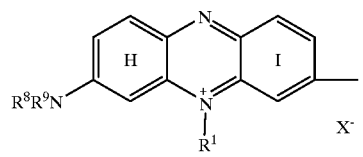

(8)

wherein $R^1$ and $R^6$ each independently represents a $C_{1-6}$ alkyl group which may have a substituent, an alkenyl group which may have a substituent or an aryl group which may have a substituent, $R^2$ and $R^3$ each independently represents a $C_{1-6}$ alkyl group which may have a substituent, an alkenyl group which may have a substituent, an aryl group which may have a substituent, $R^2$ and $R^3$ form, when taken together with the adjacent carbon atom, a 5- to 7-membered cycloalkane ring, $R^4$ represents a hydrogen atom, a $C_{1-6}$ alkyl group which may have a substituent, an alkenyl group which may have a substituent, or an aryl group which may have a substituent, $R^5$ represents a hydrogen atom, a $C_{1-6}$ alkyl group which may have a substituent, an alkenyl group which may have a substituent, an aryl group which may have a substituent, an acyl group, an alkoxycarbonyl group, a carbamoyl group, an alkylsulfonyl group or an arylsulfonyl group, Q represents a nitrogen atom or a group CR', wherein R' represents a hydrogen atom, a $C_{1-6}$ alkyl group which may have a substituent, an alkenyl group which may have a substituent or an aryl group which may have a substituent, $R^7$ represents an aralkyl group which may have a substituent or a group $CH_2$—CH(OH)—$CH_2$—OR,'' wherein R'' represents a $C_{1-6}$ alkyl group which may have a substituent, an alkenyl group which may have a substituent or an aryl group which may have a substituent, $R^8$ and $R^9$ each independently represents a $C_{1-6}$ alkyl group which may have a substituent, an alkenyl group which may have a substituent or an aryl group which may have a substituent, or $R^8$ and $R^9$ form, when taken together with the adjacent nitrogen atom, a nitrogen-containing heterocycle; $X^-$ represents an anion, and rings C, E, G, H and I may each independently have a substituent or may be cyclocondensed with another aromatic ring;

D represents a nitrogen atom or a group CR,''' wherein R''' represents a hydrogen atom or a $C_{1-6}$ alkyl group which may have a substituent; and B represents the residue of a phenol, aniline, acylacetoarylamide, pyridone, quinoline, isoquinoline, pyrazole, indole, diphenylamine, aminopyridine, pyrimidine, pyrimidone, naphthol, naphthylamine, amninothiazaole, thiophene or hydroxypyridine coupling component; the composition having a pH ranging from 6–11 that is adjusted to within said range by an alkali agent and containing at least one cosmetic ingredient selected from the group consisting of hydrocarbons, animal or vegetable fats and oils, fatty acids, organic solvents, hair penetration promoters, cationic surfactants, natural or synthetic polymers, alcohols, ethers, amphoteric surfactants, nonionic surfactants, protein derivatives, amino acids, antiseptics, chelating agents, stabilizing agents, antioxidants, plant extracts, crude drug extracts, vitamins, colorants, perfumes, aerosolizing agents and UV absorbers.

13. A method of dyeing hair, comprising:

treating the hair with a two-part aqueous formulation comprising, in a first part, a direct dye compound represented by formula (1):

A—D=D—B (1)

wherein,

A represents a group of one of the following formulas (2), (3), (4), (5), (7) or (8):

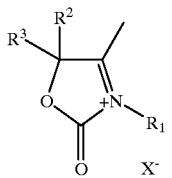
(2)

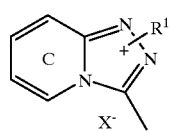
(3)

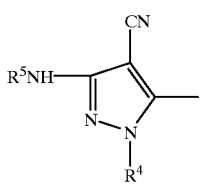
(4)

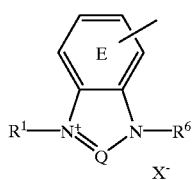
(5)

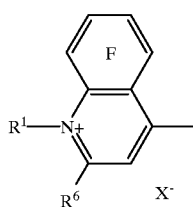
(6)

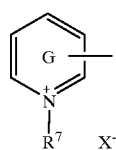
(7)

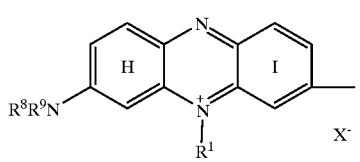
(8)

wherein $R^1$ and $R^6$ each independently represents a $C_{1-6}$ alkyl group which may have a substituent, an alkenyl group which may have a substituent or an aryl group which may have a substituent, $R^2$ and $R^3$ each independently represents a $C_{1-6}$ alkyl group which may have a substituent, an alkenyl group which may have a substituent, an aryl group which may have a substituent, $R^2$ and $R^3$ form, when taken together with the adjacent carbon atom, a 5- to 7-membered cycloalkane ring, $R^4$ represents a hydrogen atom, a $C_{1-6}$ alkyl group which may have a substituent, an alkenyl group which may have a substituent, or an aryl group which may have a substituent, $R^5$ represents a hydrogen atom, a $C_{1-6}$ alkyl group which may have a substituent, an alkenyl group which may have a substituent, an aryl group which may have a substituent, an acyl group, an alkoxycarbonyl group, a carbamoyl group, an alkylsulfonyl group or an arylsulfonyl group, Q represents a nitrogen atom or a group CR', wherein R' represents a hydrogen atom, a $C_{1-6}$ alkyl group which may have a substituent, an alkenyl group which may have a substituent or an aryl group which may have a substituent, $R^7$ represents an aralkyl group which may have a substituent or a group $CH_2$—$CH(OH)$—$CH_2$—OR," wherein R" represents a $C_{1-6}$ alkyl group which may have a substituent, an alkenyl group which may have a substituent or an aryl group which may have a substituent, $R^8$ and $R^9$ each independently represents a $C_{1-6}$ alkyl group which may have a substituent, an alkenyl group which may have a substituent or an aryl group which may have a substituent, or $R^8$ and $R^9$ form, when taken together with the adjacent nitrogen atom, a nitrogen-containing heterocycle; $X^-$ represents an anion, and rings C, E, G, H and I may each independently have a substituent or may be cyclocondensed with another aromatic ring;

D represents a nitrogen atom or a group CR,''' wherein R''' represents a hydrogen atom or a $C_{1-6}$ alkyl group which may have a substituent; and B represents the residue of a phenol, aniline, acylacetoarylamide, pyridone, quinoline, isoquinoline, pyrazole, indole, diphenylamine, aminopyridine, pyrimidine, pyrimidone, naphthol, naphthylamine, amninothiazaole, thiophene or hydroxypyridine coupling component; the first part having a pH ranging from 6–11 that is adjusted to within said range by an alkali agent; and a second part comprising an aqueous solution of an oxidizing agent.

14. A method of dyeing hair, comprising:

treating the hair with a three-part aqueous formulation comprising, in a first part, a direct dye compound represented by formula (1):

A—D=D—B  (1)

wherein,

A represents a group of one of the following formulas (2), (3), (4), (5), (7) or (8):

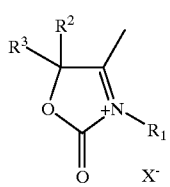
(2)

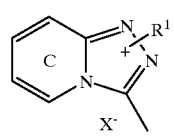
(3)

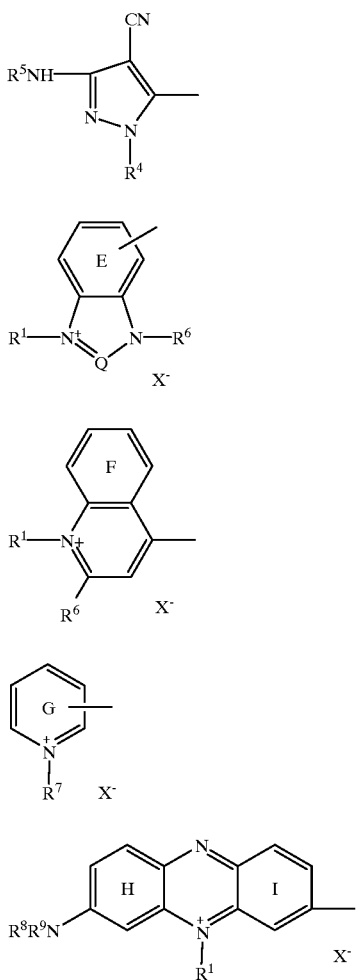

wherein $R^1$ and $R^6$ each independently represents a $C_{1-6}$ alkyl group which may have a substituent, an alkenyl group which may have a substituent or an aryl group which may have a substituent, $R^2$ and $R^3$ each independently represents a $C_{1-6}$ alkyl group which may have a substituent, an alkenyl group which may have a substituent, an aryl group which may have a substituent, $R^2$ and $R^3$ form, when taken together with the adjacent carbon atom, a 5- to 7-membered cycloalkane ring, $R^4$ represents a hydrogen atom, a $C_{1-6}$ alkyl group which may have a substituent, an alkenyl group which may have a substituent, or an aryl group which may have a substituent, $R^5$ represents a hydrogen atom, a $C_{1-6}$ alkyl group which may have a substituent, an alkenyl group which may have a substituent, an aryl group which may have a substituent, an acyl group, an alkoxycarbonyl group, a carbamoyl group, an alkylsulfonyl group or an arylsulfonyl group, Q represents a nitrogen atom or a group CR', wherein R' represents a hydrogen atom, a $C_{1-6}$ alkyl group which may have a substituent, an alkenyl group which may have a substituent or an aryl group which may have a substituent, $R^7$ represents an aralkyl group which may have a substituent or a group $CH_2$—CH(OH)—$CH_2$—OR," wherein R" represents a $C_{1-6}$ alkyl group which may have a substituent, an alkenyl group which may have a substituent or an aryl group which may have a substituent, $R^8$ and $R^9$ each independently represents a $C_{1-6}$ alkyl group which may have a substituent, an alkenyl group which may have a substituent or an aryl group which may have a substituent, or $R^8$ and $R^9$ form, when taken together with the adjacent nitrogen atom, a nitrogen-containing heterocycle; $X^-$ represents an anion, and rings C, E, G, H and I may each independently have a substituent or may be cyclocondensed with another aromatic ring;

D represents a nitrogen atom or a group CR,'" wherein R'" represents a hydrogen atom or a $C_{1-6}$ alkyl group which may have a substituent; and B represents the residue of a phenol, aniline, acylacetoarylamide, pyridone, quinoline, isoquinoline, pyrazole, indole, diphenylamine, aminopyridine, pyrimidine, pyrimidone, naphthol, naphthylamine, amninothiazaole, thiophene or hydroxypyridine coupling component; the first part having a pH ranging from 6–11 that is adjusted to within said range by an alkali agent;

a second part, comprising an aqueous solution of an oxidizing agent; and a third part, comprising a powdered oxidizing agent.

* * * * *

UNITED STATES PATENT AND TRADEMARK OFFICE
CERTIFICATE OF CORRECTION

PATENT NO.    : 6,607,563 B2
DATED         : August 19, 2003
INVENTOR(S)   : Yukihiro Ohashi et al.

It is certified that error appears in the above-identified patent and that said Letters Patent is hereby corrected as shown below:

Column 14,
Line 41, "$CH_2$-CH (OH)-$CH_2$-OR," wherein" should read -- $CH_2$-CH (OH)-$CH_2$-OR", wherein --;
Line 51, "X represents" should read -- $X^-$ represents --;
Line 55, "group CR,'" wherein" should read -- group CR'", wherein --;
Line 63, "amninothiazaole" should read -- aminothiazole --.

Column 16,
Line 32, "$CH_2$-CH (OH)-$CH_2$-OR," wherein" should read -- $CH_2$-CH (OH)-$CH_2$-OR", wherein --;
Line 41, "X represents" should read -- $X^-$ represents --;
Line 45, "group CR,'" wherein" should read -- group CR'", wherein --;
Line 53, "amninothiazaole" should read -- aminothiazole --.

Column 18,
Line 11, "$CH_2$-CH (OH)-$CH_2$-OR," wherein" should read -- $CH_2$-CH (OH)-$CH_2$-OR", wherein --;
Line 25, "group CR,'" wherein" should read -- group CR'", wherein --;
Line 33, "amninothiazaole" should read -- aminothiazole --.

Column 20,
Line 22, "$CH_2$-CH (OH)-$CH_2$-OR," wherein" should read -- $CH_2$-CH (OH)-$CH_2$-OR", wherein --;
Line 35, "group CR,'" wherein" should read -- group CR'", wherein --;
Line 44, "amninothiazaole" should read -- aminothiazole --.

Column 22,
Line 12, "$CH_2$-CH (OH)-$CH_2$-OR," wherein" should read -- $CH_2$-CH (OH)-$CH_2$-OR", wherein --;
Line 26, "group CR,'" wherein" should read -- group CR'", wherein --;
Line 35, "amninothiazaole" should read -- aminothiazole --.

UNITED STATES PATENT AND TRADEMARK OFFICE
CERTIFICATE OF CORRECTION

PATENT NO. : 6,607,563 B2
DATED : August 19, 2003
INVENTOR(S) : Yukihiro Ohashi et al.

It is certified that error appears in the above-identified patent and that said Letters Patent is hereby corrected as shown below:

Column 24,
Line 18, "$CH_2$-CH (OH)-$CH_2$-OR," wherein" should read -- $CH_2$-CH (OH)-$CH_2$-OR", wherein --;
Line 31, "group CR,'" wherein" should read -- group CR'", wherein --;
Line 38, "amninothiazaole" should read -- aminothiazole --.

Signed and Sealed this

Thirteenth Day of January, 2004

JON W. DUDAS
*Acting Director of the United States Patent and Trademark Office*